United States Patent [19]

Wehner et al.

[11] Patent Number: 4,578,489
[45] Date of Patent: Mar. 25, 1986

[54] AMMONIUM STANNATES-(IV)

[75] Inventors: Wolfgang Wehner, Zwingenberg; Reinhardt Grade, Bensheim, both of Fed. Rep. of Germany

[73] Assignee: Ciba-Geigy Corporation, Ardsley, N.Y.

[21] Appl. No.: 535,487

[22] Filed: Sep. 26, 1983

[30] Foreign Application Priority Data

Jun. 10, 1982 [CH] Switzerland .......................... 5876/82

[51] Int. Cl.$^4$ ................................................ C07F 7/22
[52] U.S. Cl. ..................................... 556/100; 556/104; 514/493; 252/8.8; 71/83; 71/97; 546/9
[58] Field of Search ...................................... 260/429.7

[56] References Cited

U.S. PATENT DOCUMENTS

| | | | |
|---|---|---|---|
| 2,580,473 | 1/1952 | Sowa .......................... | 260/429.7 X |
| 2,632,754 | 3/1953 | Albert ......................... | 260/429.7 X |
| 3,070,615 | 12/1962 | Seyferch ..................... | 260/429.7 |
| 3,201,316 | 8/1965 | Norris ......................... | 260/429.7 X |
| 3,346,607 | 10/1967 | Lombardo .................... | 260/429.7 |
| 3,397,215 | 8/1968 | Hettinger .................... | 260/429.7 X |
| 3,539,605 | 11/1970 | Oberhofer ................... | 260/429.7 X |
| 3,901,824 | 8/1975 | Knezevic et al. ............ | 260/429.7 X |
| 4,013,583 | 3/1977 | Knifton ....................... | 260/429.7 X |
| 4,036,866 | 7/1977 | Larkin et al. ................ | 260/429.7 |
| 4,374,145 | 2/1983 | Wehner et al. .............. | 260/429.7 X |

FOREIGN PATENT DOCUMENTS

| | | |
|---|---|---|
| 48696 | 9/1981 | European Pat. Off. . |
| 1204226 | 11/1965 | Fed. Rep. of Germany . |
| 1219029 | 6/1966 | Fed. Rep. of Germany . |
| 2411016 | 9/1974 | Fed. Rep. of Germany . |

OTHER PUBLICATIONS

J. W. Nicholson, Coord. Chem. Rev., 47, 263 (1982).
E. P. Oshchepkova et al, Biok . . . , 1976, 99 (German translation).

*Primary Examiner*—Helen M. S. Sneed
*Attorney, Agent, or Firm*—Luther A. R. Hall

[57] ABSTRACT

Ammonium stannates of the formula $$[(R^1)_a(R^2)_bN(R^3)_c(R^4)_d]_n^{\oplus}[(R^7)_qSnX_rY_t]_w^{n\ominus} \qquad (I)$$

in which the symbols $R^1$, $R^2$, $R^3$, $R^4$, $R^7$, X, Y, a, b, c, d, n, q, r, t and w are as defined in the description, are effective biocides. They can be used both for the protection of materials and for protecting crop plants. Their good solubility in water and their low volatility are particularly valuable properties.

6 Claims, No Drawings

AMMONIUM STANNATES-(IV)

The present invention relates to novel ammonium stannate complexes which are distinguished by a very good biocidal activity.

It is known that ammonium salts, organo-tin compounds and also certain ammonium stannates can be used as biocides.

A general review of the chemistry of the organo-stannate-(IV) complexes is given by J. W. Nicholson in Coord. Chem. Rev., 47, 263 (1982).

German Auslegeschriften Nos. 1,204,226 and 1,219,029 describe complex salts which are obtained by reacting ammonium salts with triphenyltin salts. The antimicrobial activity of the complex salts is also described in these texts. Certain ammonium stannates are described as pest control compositions in European Patent Publication No. 48,696. However, these known compounds do not meet in every respect the high requirements which are nowadays set for a biocide.

The present invention relates to compounds of the formula I

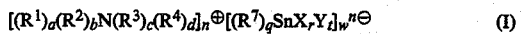
$$[(R^1)_a(R^2)_bN(R^3)_c(R^4)_d]_n^\oplus [(R^7)_qSnX_rY_t]_w^{n\ominus} \quad (I)$$

in which $R^1$ and $R^2$ independently of one another are hydrogen, $C_1$-$C_6$-alkyl, $C_1$-$C_6$-hydroxyalkyl or a polyglycol radical having a degree of polymerisation of 2 to 25, and $R^3$ is hydrogen, hydroxyl, $C_1$-$C_6$-alkyl, $C_1$-$C_6$-hydroxyalkyl, glycidyl, $C_1$-$C_6$-halogenoalkyl, phenyl, benzyl, $C_8$-$C_{22}$-alkylbenzyl, monochlorobenzyl, dichlorobenzyl, mononitrobenzyl, dinitrobenzyl, trimethoxysilylpropyl or triethoxysilylpropyl, and $R^4$ is $C_8$-$C_{22}$-alkyl, a polyglycol radical having a degree of polymerisation of 2-25, $R^5$-phenoxyethoxyethyl, $R^5$—C(0)N-H—(CH$_2$)m— or $R^5$-O-phenoxyethoxyethyl, $R^5$ being $C_1$-$C_{12}$-alkyl and m being 2 or 3, and $R^4$ is also a group of the formula II

$$-Z-(R^1)N(R^2)R^3 \quad (II)$$

in which Z is a linear or branched ($C_vH_{2v}$)group, v being a number from 2 to 22, it being possible for this group to be interrupted once or repeatedly by —O—, —S—, —N(R$^6$)—, —C(O)—O— or —O—C(O)—, and $R^6$ is hydrogen or $C_1$-$C_4$-alkyl, and $R^1$ $R^2$ and $R^3$ are as defined above, and, furthermore, two of the radicals $R^1$, $R^2$, $R^3$ and $R^4$ together with the nitrogen atom to which they are attached, form a saturated or partially unsaturated heterocyclic ring which is unsubstituted or substituted by one or two methyl or ethyl groups, or three of the radicals $R^1$, $R^2$, $R^3$ and $R^4$, together with the nitrogen atom to which they are attached, form an unsaturated heterocyclic ring which is unsubstituted or substituted by one or two methyl, ethyl, hydroxyl or acetyl groups, and $R^7$ is $C_3$-$C_5$-alkyl or benzyl the latter being substituted by a hydroxyl or cyano group or by one or two $C_2$-$C_{22}$-alkoxycarbonyl or $C_2$-$C_{22}$-alkylcarbonyloxy groups or by a halogen atom, or, subject to the proviso that X and/or Y is fluorine, $R^7$ is phenyl, and in which X and Y independently of one another are fluorine, chlorine, bromine, iodine, cyanate, thiocyanate or carboxylate of the form $R^8$—COO—, $R^8$ being hydrogen or linear or branched $C_1$-$C_{18}$-alkyl which is unsubstituted or substituted by one to three halogen atoms or by one to three hydroxyl or ammonium groups, or being phenyl which is unsubstituted or substituted by one to three halogen atoms or by one to three amino, nitro, hydroxyl or $C_1$-$C_4$-alkoxy groups, or being $C_5$-$C_8$-cycloalkyl or a substituted or unsubstituted pyridine radical, and in which a, b, c and d are integers having the values 1 or 4, subject to the proviso that the total (a+b+c+d) is 4 and subject to the proviso that a, b, c or d can only assume a value of 4 if X and/or Y is fluorine and if, at the same time, q is 1, 2 or 3, and in which, finally, n is 1 or 2 and q is 0, 1, 2 or 3, r and t are an integer from 0 to 5, the total (q+r+t) having the value (n+4) and, in the event that q=1, 2 or 3, the total (r+t) being 2 to 5, and, if $R^4$ is a group of the formula II, w is 2 and otherwise is 1.

Examples of $R^1$, $R^2$ and $R^3$ as $C_1$-$C_6$-alkyl are linear or branched alkyl radicals, such as methyl, ethyl, n-propyl, isopropyl, n-butyl, sec.-butyl, n-amyl, isoamyl or n-hexyl.

Examples of $R^1$, $R^2$ and $R^3$ as $C_1$-$C_6$-hydroxyalkyl are methylol, 2-hydroxyethyl, 3-hydroxypropyl or 6-hydroxyhexyl.

Examples of $R^3$ as $C_1$-$C_6$-halogenoalkyl and, preferably, $C_1$-$C_2$-halogenoalkyl are chloromethyl, 2-bromoethyl or 6-chlorohexyl. Halogen is preferably chlorine. Radicals such as 2-hydroxy-3-chloropropyl should also be mentioned.

$R^3$ is substituted or unsubstituted benzyl, such as o-, m- or p-methylbenzyl, 2,3-, 2,4-, 3,5- or 2,5-dimethylbenzyl, nonylbenzyl, laurylbenzyl, tetradecylbenzyl, o-, m- or p-chlorobenzyl, 2,3-, 3,4-, 3,5- or 2,5-dichlorobenzyl, o-, m- or p-nitrobenzyl or 2,3-, 3,4-, 3,5- or 2,5-dinitrobenzyl.

As $C_8$-$C_{22}$-alkyl, $R^4$ can be n-octyl, 2-ethylhexyl or branched or unbranched nonyl, decyl, undecyl, dodecyl, tridecyl, tetradecyl, hexadecyl, octadecyl, eicosyl or docosyl.

Examples of $R^5$ as $C_1$-$C_{12}$-alkyl are methyl, ethyl, n-propyl, n-butyl, sec.-butyl, n-hexyl, n-octyl, 2-ethylhexyl, 1,1,3,3-tetramethylbutyl or linear or branched nonyl, decyl or dodecyl.

If $R^4$ is a group of the formula II, Z is, for example: ethylene or 1,3-trimethylene, 1,4-tetramethylene, or propylidene, —CH$_2$CH$_2$—O—CH$_2$CH$_2$—, —(CH$_2$CH$_2$O)$_4$—CH$_2$CH$_2$—, —CH$_2$CH$_2$—N-H—CH$_2$CH$_2$— or —CH2—COOCH$_2$CH$_2$—.

Examples of $R^6$ as $C_1$-$C_4$-alkyl are methyl, ethyl, n-propyl, isopropyl or n-butyl.

A saturated or partially saturated heterocyclic ring which is unsubstituted or substituted by one or two methyl groups and is formed by two of the radicals $R^1$, $R^2$, $R^3$ and $R^4$, together with the nitrogen atom, is, for example, pyrrolidine, piperidine, 2-methylpiperidine, piperazine, 2,5-dimethylpiperazine or morpholine.

An unsaturated heterocylic ring which is unsubstituted or substituted by one or two methyl or ethyl groups and which is formed by three of the radicals $R^1$, $R^2$, $R^3$ and $R^4$, together with the nitrogen atom, can be pyridine, 4-methylpyridine, quinoline, pyrimidine, thiazole, imidazole or oxazole.

Examples of $R^7$ as $C_3$-$C_5$-alkyl are n-propyl, isopropyl, sec.-butyl, n-amyl or, preferably, n-butyl, and, as substituted benzyl which is, for example, substituted in the o-, m- or p-position, examples are hydroxybenzyl, cyanobenzyl, ethoxybenzyl, octadecyloxybenzyl, methylcarbonyloxybenzyl or octadecylcarbonyloxybenzyl.

Examples of $R^8$ as $C_1$-$C_{18}$-alkyl are methyl, ethyl, n-propyl, isopropyl, m-butyl, sec.-butyl, tert.-butyl, n-amyl, isoamyl, n-hexyl, n-octyl, n-decyl, n-dodecyl, n-tetradecyl, n-hexadecyl or n-octadecyl. Examples of $R^8$ as $C_5-C_8$-cycloalkyl are cyclopentyl, cyclohexyl, cycloheptyl or cyclooctyl, cyclopentyl being preferred. Examples of $R^8$ as substituted $C_1-C_{18}$-alkyl are methylol, 2-hydroxyethyl, 4-hydroxybutyl, 6-hydroxyhexyl, 2-hydroxyoctadecyl, chloromethyl, 2-chloroethyl, 1,2-dichloroethyl, 4-chlorobutyl, 6-chlorohexyl, 2-chlorooctadecyl, aminomethyl, 2-aminoethyl, 4-aminobutyl, 6-aminohexyl or 2-aminooctadecyl. Examples of $R^5$ as substituted phenyl are o-, m- or p-substituted chlorophenyl, aminophenyl, nitrophenyl, methoxyphenyl, ethoxyphenyl, n-propoxyphenyl or n-butoxyphenyl, or 2,3-, 3,4-, 3,5- or 2,5-dichlorophenyl, dinitrophenyl, diaminophenyl, dimethoxyphenyl, diethoxyphenyl, di-n-propoxyphenyl or di-n-butoxyphenyl, or 2-chloro-3-nitrophenyl or 3-amino-4-ethoxyphenyl, 3-amino-5-ethoxyphenyl or 2,4,6-triaminophenyl or 2,4,6-trichlorophenyl.

Preferred compounds of the formula I are those in which q is 0 or in which q is 1, 2 or 3 or in which, in particular, q is 3.

Compounds of the formula I in which X and/or Y is fluorine and/or chlorine are also of interest.

Preferred compounds of the formula I are those in which $R^1$, $R^2$ and $R^3$ independently of one another are hydrogen, $C_1-C_6$-alkyl or $C_1-C_2$-hydroxyalkyl and $R^3$ is additionally phenyl, benzyl, $C_8-C_{22}$-alkylbenzyl, monochlorobenzyl, dichlorobenzyl, mononitrobenzyl, dinitrobenzyl or trimethoxysilylpropyl, and $R^4$ is a radical of the formula II in which $R^6$ is hydrogen or methyl and v is a number from 2 to 10, and $R^4$ can also have the other definitions indicated above, and, furthermore, two of the radicals $R^1$, $R^2$, $R^3$ and $R^4$, together with the nitrogen atom, are pyrrolidine, piperidine, piperazine or morpholine which is unsubstituted or substituted by one or two methyl or ethyl groups, or three of the radicals $R^1$, $R^2$, $R^3$ and $R^4$, together with the nitrogen atom, are pyridine, quinoline, pyrimidine, thiazole, oxazole or imidazole which is unsubstituted or substituted by one or two methyl or ethyl groups, and Y is fluorine or chlorine.

Compounds of the formula I which are of interest are those in which $R^1$ and $R^2$ independently of one another are $C_1-C_6$-alkyl or methylol and $R^3$ is $C_1-C_6$-alkyl, methylol, phenyl, benzyl, $C_8-C_{22}$-alkylbenzyl, monochlorobenzyl, dichlorobenzyl, mononitrobenzyl or dinitrobenzyl, and $R^4$ is p-1,1,3,3-tetramethylbutylphenoxyethoxyethyl, $C_{12}-C_{16}$-alkyl or a group of the formula II in which $R^6$ is hydrogen and v is a number from 2 to 10, and, furthermore, the radicals $R^1$, $R^2$, $R^3$ and $R^4$ form a heterocyclic ring of the type defined above as preferred.

Compounds of the formula I which are particularly preferred are those in which two of the radicals $R^1$, $R^2$, $R^3$ and $R^4$, together with the nitrogen atom to which they are attached, form a saturated or partially unsaturated heterocyclic ring which is unsubstituted or substituted by one or two methyl or ethyl groups, or three of the radicals $R^1$, $R^2$, $R^3$ and $R^4$ together with the nitrogen atom to which they are attached, form an unsaturated heterocyclic ring which is unsubstituted or substituted by one or two methyl or ethyl groups.

In addition, compounds of the formula I which are particularly preferred are those in which $R^1$, $R^2$ and $R^3$ independently of one another are $C_1-C_6$-alkyl or methylol, and $R^3$ is also benzyl, $C_8-C_{22}$-alkylbenzyl, monochlorobenzyl, dichlorobenzyl, mononitrobenzyl or dinitrobenzyl, and $R^4$ is $C_8-C_{16}$-alkyl.

Compounds of the formula I which are also of interest are those in which $R^4$ is a group of the formula II in which $R^6$ is hydrogen or methyl and v is a number from 2 to 10.

Compounds of the formula I which should be singled out particularly are those in which $R^1$ and $R^2$ independently of one another are $C_1-C_6$-alkyl or methylol, and $R^3$ is $C_1-C_6$-alkyl, methylol, benzyl, $C_8-C_{22}$-alkylbenzyl, monochlorobenzyl, dichlorobenzyl, mononitrobenzyl or dinitrobenzyl, and $R^4$ is $C_8-C_{16}$-alkyl or a group of the formula II in which $R^6$ is hydrogen and v is a number from 2 to 6.

Compounds of the formula I in which n is 1 are preferred.

Compounds of the formula IV

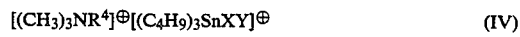
$$[(CH_3)_3NR^4]^{\oplus}[(C_4H_9)_3SnXY]^{\ominus} \qquad (IV)$$

in which the radical $R^4$ is $C_{12}-C_{18}$-alkyl and X and/or Y is chlorine or fluorine are also of interest.

Compounds of the formula V

$$[(CH_3)_2NR_2^4]^{\oplus}[(C_4H_9)_3SnXY]^{\ominus} \qquad (V)$$

in which the radical $R^4$ is $C_{12}-C_{18}$-alkyl and X and/or Y is chlorine or fluorine are also preferred.

Compounds of the formula VI

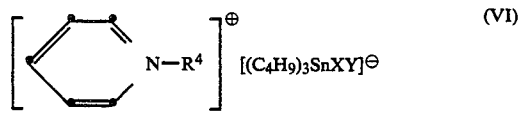

in which the radical $R^4$ is $C_{12}-C_{18}$-alkyl and X and/or Y is chlorine or fluorine are also of interest.

The compound dimethyl-benzyl-n-tetradecylammonium tri-n-butyldichlorostannate (IV) is particularly preferred.

The compound dimethyl-benzyl-n-tetradecylammonium tri-n-butyldifluorostannate-(IV) is also preferred.

The ammonium stannates of the present invention can be prepared, for example, by reacting approximately n/w mol of an ammonium salt of the formula III

$$[(R^1)_a(R^2)_bN(R^3)_c(R^4)_d]X_p \qquad (III)$$

in which $R^1$, $R^2$, $R^3$, $R^4$, a, b, c, d, n, w and X are as defined above and, if $R^4$ is a group of the formula II, p is 2 and is otherwise 1, with approximately one mol of a tin salt of the formula $(R^7)_qSnY_t$ (VII) in which $R^7$, Y, q and t are as defined above.

The ammonium salts of the formula III and the tin salts of the formula VII are, as a rule, commercially available products or they can be prepared by known methods.

The reaction of the ammonium salts of the formula III with the tin salt of the formula VII is advantageously carried out at room temperature with or without a solvent (in a homogeneous phase or in 2 phases), for instance methanol, ethanol, water, chloroform, acetone, methylene chloride, toluene, xylene etc. If a solvent is concomitantly used, it can be removed by evaporation after the reaction, or the reaction product is precipitated, for example by adding an ether, and the product thus obtained is purified, for example by recrystallisation.

The following are examples of ammonium salts of the formula III: dimethyl-lauzylammonium chloride, dimethyl-n-octylammonium chloride, dimethyl-n-decylammonium chloride, benzimidazolium-N-methyl-N-stearyl chloride, dimethyl-laurylglycidylammonium chloride, tributy-tetradecylammonium chloride, dihydroxyethyl-n-lauryl-benzylammonium chloride, dimethyl-n-tetradecyl-benzylammonium chloride, trimethyl-n-hexadecylammonium chloride, dimethyl-n-hexadecyl-benzylammonium chloride, dimethyl-phenylammonium chloride, dodecyl-(2-methyl-5-ethyl)pyridinium bromide, piperidinium chloride, trimethyl-dodecylammonium bromide, N-methyl-piperidinium chloride, N-methyl- N-ethylmorpholinium bromide, N-decyl-laurylimidazolium bromide, benzyl-dimethyl-(p-1,1,3,3-tetramethylbutyl-phenoxyethoxyethyl)-ammonium chloride, 3-(trimethyoxysilyl)-propyl-dimethyloctadecylammonium chloride, trimethylol-n-tetradecylammonium chloride, hexamethylene-di-(dimethyl-n-dodecylammonium chloride), tetramethylene-di-(dimethyl-n-tetradecylammonium bromide), tetramethylene-di-(4-methyl-pyridinium chloride), hexamethylene-di-pyridinium chloride, tetramethylene-di-(N-methylmorpholinium bromide), bis-polyglycol-laurylammonium chloride (n=2-25), tris-polyglycol-benzylammonium chloride (n=2-25), 5-acetyl-8-hydroxy-N-lauryl-quinolinium bromide, tris-hydroxyethyl-laurylammonium bromide, monolaurylammonium chloride and dodecamethylene-di-ammonium chloride.

The following are examples of tin salts of the formula VII: tri-(n-butyl)-tin fluoride, tri-(n-buty)-tin chloride, tri-(n-butyl)-tin bromide, tri-(n-butyl)-tin iodide, di-(n-butyl)-tin difluoride, di-(n-butyl)-tin dichloride, n-butyl-tin trifluoride, n-butyltin trichloride, tri-(n-propyl)-tin chloride, tri-(n-amyl)-tin fluoride, tri-(n-butyl)-tin rhodanide, tri-(n-butyl)-tin benzoate, tri-(n-butyl)-tin propionate, tri-(n-butyl)-tin naphthenate and tin tetrachloride.

The compounds of the formula I are distinguished by low volatility and good solubility in water.

The compounds according to the invention provide a broad spectrum of action for the control of animal and plant pests; this leads to a variety of possible uses, for example as bactericides or disinfectants, against the formation of slime in paper manufacture, as fungicides, insecticides, acaricides or herbicides and also as algicides. In addition, the novel substances are excellently suitable for use as industrial antimicrobial agents for the protection of materials, for example protecting wood, cellulose and paper, textiles and leather, dyes, paints, anti-fouling paints and similar coating materials, optical and other types of glass, cooling water, plastics, rubber and adhesives, drilling and cutting oils, petroleum, lubricants, waxes and fuels and other materials, and especially for protecting biodegradable plastics and plastics compositions, preferably plasticised polyvinyl chloride or polyvinylidene chloride.

Depending on the purpose for which they are used, the compounds are employed within the ranges of concentrations known to those skilled in the art. The limits of customary concentrations are given by the following values: whereas in cooling water concentrations as low as the ppm range are sufficient, concentrations of up to 40% by weight are customary in anti-fouling formulations.

The compounds can be applied in a pure form or, together with carriers, as dusting agents, sprinkling agents or misting agents. They can also be suspended in liquid brushing agents and the like, in which connection, if necessary for the formation of uniform dispersions, wetting agents or emulsifiers can promote the uniform distribution of the active compound. Further biocides, such as insecticides, can be added.

A preferred field of use comprises protective coatings, in particular anti-fouling paints, based on organic materials and containing, in addition to the customary primary materials and additives, 0.5–60 % by weight, preferably 3–25 % by weight, based on the total mixture, of a compound of the formula I or mixtures thereof.

Customary primary materials for anti-fouling paints are the paint raw materials designated binders and known to those skilled in the art, such as natural and synthetic resins, homopolymeric and copolymeric products containing the monomers vinyl chloride, vinylidene chloride, styrene, vinyltoluene, vinyl esters, acrylic acids and methacrylic acid and esters thereof, and also chlorinated rubber, natural and synthetic rubber, if appropriate chlorinated or cyclised, and also reactive resins, such as epoxide resins, polyurethane resins and unsaturated polyesters which can, if appropriate, be converted by the addition of curing agents into film-forming, higher-molecular products.

The binders can be liquid or can be present in a dissolved form. In the case of dissolved binders, and also thermoplastics, it is also possible to form a protective film by evaporating the solvent. Solid coating agents can be applied to objects, for example by the powder coating process. Examples of further customary primary materials are tar, modifiers, dyes, inorganic or organic pigments, fillers and curing agents.

It has also been found that compounds having the structure of the formula I possess a microbicidal spectrum for the protection of crop plants which is very advantageous for practical requirements. Examples of crop plants within the scope of the present invention are cereals, maize, rice, vegetables, sugar beet, soya, groundnuts, fruit trees, ornamental plants, vines, hops, cucurbitacae (cucumbers, pumpkins and melons), solanaceae, such as potatoes, tobacco and tomatoes, and also banana, cocoa and natural rubber plants.

The active compounds of the formula I make it possible to inhibit or destroy the fungi or bacteria which occur on plants or parts of plants (fruit, flowers, foliage, stalks, tubors or roots) of these and related crops, and parts of plants which grow later also remain protected from microorganisms of this type. The active compounds are effective against phytopathogenic fungi belonging to the following classes: Ascomycetes (for example Erysiphaceae or Fusarium); Basidiomycetes, such as Puccinia or Fungi imperfecti (for example Cercospora or Septoria); and Phytomycetes, such as Phytophthora. In addition, the compounds of the formula I have a systemic action. The compounds of the formula I are advantageously employed as dressing agents for treating seed and stored products (fruit, tubers or grains) and plant cuttings to protect them against fungal infestations and also against phytopathogenic fungi which occur in the soil.

Additionally, they are effective against phytopathogenic bacteria, for example Pseudomonas sp. and Xanthomonas sp.

The compounds of the formula I are used in plant protection on their own or together with suitable carriers and/or other adjuvants. Suitable carriers and adjuvants can be solid or liquid and correspond to the substances conventionally used in the art of formulation, for example natural or regenerated mineral substances, solvents, dispersing agents, wetting agents, tackifiers, thickeners, binders or fertilisers.

The content of active compound in commercial agents is between 0.1 and 90 %.

For application, the compounds of the formula I can be processed to the following formulations (the weight percentages in brackets represent advantageous quantities of active compound):

Solid formulations: dusting agents and sprinkling agents (up to 10 %), granules, coated granules, impregnated granules and homogeneous granules and pellets (grains) (1 to 80 %).

Liquid formulations:

(a) active compound concentrates which are dispersible in water:

wettable powders and pastes (25-90 % in a commercial pack; 0.01 to 15 % in a ready-to-use solution) and emulsion and solution concentrates (10 to 50 %; 0.01 to 15 % in a ready-to-use solution);

(b) solutions (0.1 to 20 %); aerosols.

The invention thus also embraces agents containing the compounds according to the invention and also the use of the compounds and agents according to the invention for the control of microorganisms and algae.

The biocidal mixtures which can be used in accordance with the invention can also contain further active sub- stances.

Examples of these are: a) organo-sulfur compounds, for example methylene dithiocyanate (MBT), isothiazolones or 3,5-dimethyltetrahydro-1,3,5-2H-thiadiazine-2-thione (DMTT). Such substances are employed especially against the formation of slime in paper manufacture.

(b) Chlorinated phenols, such as sodium pentachlorophenolate. Such compounds are distinguished by a broad spectrum of action.

(c) Copper salts, such as copper sulfate, in small quantities are effective algicides.

(d) 2,2-Dibromo-3-nitrilopropionamide (DBNPA) as an algicide, fungicide and bactericide.

(e) Chlorine and bromine are known, effective algicides and bactericides and are used especially in the treatment of water.

(f) In water, chlorine dioxide, chloroisocyanurates and hypochlorites are also customary biocides.

(g) Known wood biocides
a. Salt mixtures based on
silicofluorides
hydrogen fluorides
inorganic boron compounds
chromates
fluorides
arsenic (oxide or arsenates)
copper salts (sulfate or naphthenate)
tin and zinc salts
mercury compounds
b. Tar oil preparations
c. Organic active compounds:
pentachlorophenol
phenol
DDT
dieldrin
lindane or gammexane
chlorinated naphthalenes
  (h) Known disinfectants
a. Phenol or phenol derivatives
b. Formaldehyde and/or other aldehydes or derivatives
c. Chlorine or organic or inorganic substances containing active chlorine.
d. Amphoteric surfactants.

In addition, further substances and assistants such as are customarily used concomitantly in preparations of this type can, of course, also be present in such formulations. These include, for example, cationic or nonionic surface-active substances, electrolytes, complexing agents, solubilisers and dyes and aroma substances. These additives are used, for example, to improve the wetting power and resistance to hardening, for adjusting the viscosity and for increasing the stability under cold conditions, of the solutions.

The following examples illustrate the invention without limiting its scope. The percentages (%) and parts quoted in the examples are by weight.

EXAMPLE 1

Preparation of dimethyl-benzyl-tetradecylammonium tributyldichlorostannate-(IV) or dimethyl-didecylammonium tributyldichlorostannate-(IV)

18.4 parts of dimethyl-benzyl- tetradecylammonium chloride or 17.4 parts of dimethyl-didecylammonium chloride are dissolved in 80.0 parts of ethanol or chloroform. A solution of 16.3 parts of tributyltin chloride in 100 parts of ethanol or chloroform is added to this solution. After the volatile constituents have been removed, the substances remain as a residue of viscous or waxlike substances. In the $^{119}$Sn NMR spectrum, the CDCl$_3$ solutions exhibit shifts of 124.4 (Example 2) and 198.0 (Example 4) ppm towards a higher region, compared with tributyltin chloride.

EXAMPLES 2-32

The compounds listed in Table A below can also be prepared analogously, methanol, ether, THF, DMF, acetone or methylcellosolve also being suitable as solvents, depending on the solubility of the ammonium or organo-tin halides.

TABLE A

| Example | Ammonium cation[a] | Stannate anion[a] | Tin[b] NMR shift in CDCl$_3$ (ppm) | Properties or melting point (°C.) |
|---|---|---|---|---|
| 1 | Tri-butyl-tetradecyl | Tri-n-butyldichloro | — | viscous oil |
| 2 | Dimethyl-benzyl-tetradecyl | Tri-n-butyldichloro | −124,4 | viscous oil |
| 3 | Dimethyl-benzyl-tetradecyl | Tributyldifluoro | — | >300 |
| 4 | Dimethyl-didecyl | Tributyldichloro | −198,0 | viscous oil |

TABLE A-continued

| Example | Ammonium cation[a] | Stannate anion[a] | Tin[b] NMR shift in CDCl$_3$ (ppm) | Properties or melting point (°C.) |
|---|---|---|---|---|
| 5 | Dihydroxyethyl-benzyl-lauryl | Tributyldichloro | −89,9 | viscous oil |
| 6 | Pyridine-N—lauryl | Tributyldichloro | −134,3 | viscous oil |
| 7 | Pyridine-N—hexadecyl | Tributyldichloro | −155,1 | viscous oil |
| 8 | Dimethyl-benzyl-tetradecyl | Tributylfluorochloro | −46,0[c] | viscous oil |
| 9 | (CH$_3$)$_2$(C$_{18}$H$_{37}$)N(CH$_2$)$_3$—Si(OCH$_3$)$_3$ | Tributyldichloro | −59,4 | viscous oil |
| 10 | Trishydroxyethyl-lauryl | Tributylbromochloro | — | viscous oil |
| 11 | Trimethyl-tetradecyl | Tributyldichloro | — | viscous oil |
| 12 | Dimethyl-lauryl | Tributyldichloro | −95,9 | viscous oil |
| 13 | (structure: 8-hydroxyquinoline-N-lauryl with COCH$_3$ substituent) | Tributyldichloro | — | viscous oil |
| 14 | (CH$_3$)$_2$N(OH)C$_{12}$H$_{25}$ | Tributyldichloro | −49,5 | viscous oil |
| 15 | (CH$_3$)$_2$N(OH)C$_{16}$H$_{37}$ | Tributyldichloro | −39,2 | wax |
| 16 | (CH$_3$)$_3$NC$_{12}$H$_{25}$ | Tributyldichloro | −148,8 | viscous oil |
| 17 | (CH$_3$)$_3$NC$_{16}$H$_{33}$ | Tributyldichloro | −141,8 | wax |
| 18 | (CH$_3$)$_3$NC$_{18}$H$_{37}$ | Tributyldichloro | −127,9 | wax |
| 19 | (2-heptadecyl-1-benzyl-benzimidazole, NH) | Tributyldichloro | −60,0 | viscous oil |
| 20 | (2-heptadecyl-1-methyl-benzimidazole, NH) | Tributyldichloro | −71,9 | viscous oil |
| 21 | C$_{14}$H$_{29}$(CH$_3$)$_2$—NCH$_2$—CHOH—CH$_2$OH | Tributyldichloro | −96,8 | viscous oil |
| 22 | (CH$_3$)$_3$NC$_{16}$H$_{33}$ | Tributyldifluoro | | viscous oil |
| 23 | (CH$_3$)$_3$N(CH$_2$)$_6$N(CH$_3$)$_3$ | Tributyldichloro | | 294° |
| 24 | Di-hydroxyethyl-benzyl-tetradecyl | Tributyldichloro | −89,9 | viscous oil |
| 25 | Dimethyl-dioctyl | Tributyldichloro | | viscous oil |
| 26 | (CH$_3$)$_2$(C$_{14}$H$_{29}$)N(CH$_2$—CH—CH$_2$) (epoxide ring) | Tributyldichloro | −51,6 | viscous oil |
| 27 | Tetrabutyl | Tributylchlorofluoro | −43,7[c] | 149–150 |
| 28 | Tetrabutyl | Tributyldifluoro | −100,7[c] | 187–188 |
| 29 | (C$_{12}$H$_{25}$CO)NH(CH$_2$)$_3$N(OH)—(CH$_3$)$_2$ | Tributyldichloro | −31,1 | viscous oil |
| 30 | (C$_{12}$H$_{25}$CO)NH(CH$_2$)$_3$N—(CH$_3$)$_2$(CH$_2$CONH$_2$) | Tributyldichloro | | viscous oil |

TABLE A-continued

| Example | Ammonium cation[a] | Stannate anion[a] | Tin[b] NMR shift in CDCl$_3$ (ppm) | Properties or melting point (°C.) |
|---|---|---|---|---|
| 31 | Pyridine-N—lauryl | Triphenylchlorofluoro | | 283–285 |
| 32 | Dimethyl-benzyl-tetradecyl | Tributylchlorodichloracetate | 61,8[d] | highly viscous resin |

[a]butyl = n-butyl
decyl = n-decyl
lauryl = n-dodecyl
tetradecyl = n-tetradecyl
[b]against Bu$_3$SnCl as an external standard
[c]against Bu$_3$SnF as an external standard
[d]against Bu$_3$Sn—(CHCl$_2$COO) as an external standard

EXAMPLE 33

Determination of the minimum inhibitory concentration against bacteria

Overnight cultures, grown in Caso peptone bouillon (Merck) of the various strains of bacteria: (A) *Proteus vulgaris*, (B) *Pseudomonas aeruginosa*, (C) *Enterobacter aerogenes*, (D) *Serratia marcencens*, (E) *Alcaligenes denitrificans* and (F) *Bacillus subtilis* are each diluted in a ratio of 1/1000 in saline solution. Sufficient of the suspensions is put into Caso peptone bouillon to dilute the bacteria again in the ratio of 1/1000. Each of the compounds listed in Table 1 is then added in amounts of 100 and 300 mg/liter. After being incubated for 24 hours at 30° C. in a shaking waterbath, the turbidity of the samples is evaluated. The minimum inhibitory concentration (MIC) is the concentration at which the bouillon does not become cloudy as the result of bacterial growth.

The result is illustrated in Table 1 below:

TABLE 1

| Substance No. | Determination of the MIC against bacteria Strain | | | | | |
|---|---|---|---|---|---|---|
| | A | B | C | D | E | F |
| 2 | 100 | 100 | 100 | 100 | 100 | 100 |
| 4 | 100 | 100 | 100 | 100 | 100 | 100 |
| 5 | 100 | 100 | 100 | 100 | 100 | 100 |
| 6 | 100 | 100 | 100 | 100 | 100 | 100 |
| 7 | 100 | 100 | 100 | 100 | 100 | 100 |
| 8 | 100 | 100 | 100 | 100 | 100 | 100 |
| 14 | 100 | 100 | >300 | 300 | 300 | 100 |
| 15 | 100 | 100 | >300 | >300 | 300 | 100 |
| 16 | 100 | 100 | 100 | 100 | 100 | 100 |
| 19 | 100 | 100 | >300 | >300 | 300 | 100 |
| 20 | 100 | 100 | 100 | 100 | 100 | 100 |
| 21 | 100 | 100 | 100 | 100 | 100 | 100 |
| 23 | 100 | 100 | 300 | >300 | 300 | 100 |
| 24 | 100 | 100 | 100 | 100 | 100 | 100 |
| 26 | 100 | 100 | 100 | 100 | 100 | 100 |
| 29 | 100 | 100 | >300 | >300 | 300 | 100 |
| 30 | 100 | 100 | 100 | 100 | 100 | 100 |

The good growth-inhibiting action of the compounds, in particular also against Gram-negative bacteria, which are difficult to control, can be seen from Table 1.

EXAMPLE 34

Determination of the Minimum Killing Concentration Against a Mixed Culture of Bacteria The mixed culture is prepared by putting into Tyrode sufficient of overnight cultures, grown in Caso peptone bouillon, of each of the various strains of bacteria:
(G) *Escherichia coli*
(H) *Bacillus cereus var. mycoides*
(I) *Staphylococcus aureus*
(B) *Pseudomonas aeruginosa*
(C) *Enterobacter aerogenes*
(A) *Proteus vulgaris* to give a final dilution of 1/1000 or 1/10,000, and the mixed culture is incubated for 5 hours at 30° C. in a shaking waterbath.

5 μl are then taken from the samples and added dropwise to Caso peptone agar. Growth is evaluated visually after incubating for a further 24 hours at 30° C.

As can be seen from Table 2 below, some of the compounds are also highly effective against these muciferous bacteria.

TABLE 2

Destruction of a mixed culture of bacteria diluted in a ratio of 1/1000 or 1/10,000 in Tyrode

| | Growth (mg/l) | | | | | | | | | |
|---|---|---|---|---|---|---|---|---|---|---|
| | 5 | | 10 | | 30 | | 60 | | 100 mg/l | |
| No. | 1/1000 | 1/10000 | 1/1000 | 1/10000 | 1/1000 | 1/10000 | 1/1000 | 1/10000 | 1/1000 | 1/10000 |
| 2 | + | + | + | + | (+) | − | (+) | − | (−) | − |
| 4 | + | + | + | (+) | + | − | (+) | − | (+) | − |
| 5 | + | + | + | + | + | + | + | + | + | (+) |
| 6 | + | + | + | + | + | + | + | + | + | + |
| 7 | + | + | + | (+) | (+) | (−) | − | − | − | − |
| 8 | − | − | − | − | (+) | − | (+) | − | (−) | − |
| 17 | + | (+) | + | (+) | (+) | − | − | − | − | − |
| 18 | + | (+) | + | (−) | (+) | − | (+) | − | (−) | − |

TABLE 2-continued

Destruction of a mixed culture of bacteria diluted in a ratio of 1/1000 or 1/10,000 in Tyrode

| | Growth (mg/l) | | | | | | | | | |
|---|---|---|---|---|---|---|---|---|---|---|
| | 5 | | 10 | | 30 | | 60 | | 100 mg/l | |
| No. | 1/1000 | 1/10000 | 1/1000 | 1/10000 | 1/1000 | 1/10000 | 1/1000 | 1/10000 | 1/1000 | 1/10000 |
| 24 | + | + | + | + | + | + | + | (+) | + | — |

+ = growth, no destruction
(+) = growth less than that of control (>10 colonies), slight destruction
(−) = slight growth (1–10 colonies)
− = no growth, destruction

EXAMPLE 35

Determination of the minimum inhibitory concentration against fungi

The invention is carried out using the known agar incorporation test in the following fungi:
(K) *Aspergillus niger*
(L) *Aspergillus phoenicis*
(M) *Penicillium funiculosum*
(N) *Alternaria alternata*
(O) *Cladosporium cladosporioides*
(P) *Candida albicans*
(Q) *Endomyces geotrichum*
(R) *Aureobasidium pullulans*
(S) *Chaetomium globosum* in a malt extract/agar (Merck). Inhibition is effected by adding sufficient of each of the various compounds to give final concentrations in the agar of 2, 5, 10, 50 and 100 mg/liter. The concentrations (mg/liters) required to inhibit the growth of the fungi (starting from traces of fungi added dropwise) are illustrated in Table 3.

TABLE 3

Determination of MIC against fungi (concentration in mg/liter)

| | Strain | | | | | | | | |
|---|---|---|---|---|---|---|---|---|---|
| No. | K | L | M | N | O | P | Q | R | S |
| 2 | 2 | 2 | 2 | 2 | 2 | 5 | 5 | 2 | 2 |
| 4 | 2 | 5 | 5 | 2 | 5 | 5 | 5 | 2 | 2 |
| 5 | 5 | 5 | 5 | 5 | 2 | 5 | 5 | 2 | 2 |
| 6 | 2 | 2 | 5 | 2 | 2 | 5 | 5 | 2 | 2 |
| 7 | 2 | 10 | 10 | 5 | 2 | 5 | 5 | 2 | 2 |
| 8 | ≦10 | ≦10 | ≦10 | ≦10 | ≦10 | ≦10 | ≦10 | ≦10 | ≦10 |
| 14 | 2 | 2 | 5 | 2 | 2 | 5 | 10 | 2 | 2 |
| 15 | 2 | 2 | 5 | 2 | 2 | 5 | 10 | 2 | 2 |
| 16 | 2 | 2 | 5 | 2 | 2 | 5 | 50 | 2 | 2 |
| 17 | 2 | 2 | 5 | 2 | 2 | 5 | 10 | 2 | 2 |
| 18 | 2 | 2 | 5 | 2 | 2 | 5 | 10 | 2 | 2 |
| 19 | 10 | 10 | 50 | ≦5 | 10 | 10 | 50 | 10 | ≦5 |
| 20 | 10 | 10 | 10 | ≦5 | 10 | ≦5 | 10 | 10 | ≦5 |
| 21 | ≦5 | ≦5 | ≦5 | ≦5 | ≦5 | ≦5 | ≦5 | ≦5 | ≦5 |
| 23 | 10 | 10 | 10 | ≦5 | ≦5 | ≦5 | 10 | ≦5 | ≦5 |
| 24 | 5 | 5 | 5 | 5 | 2 | 5 | 5 | 2 | 2 |
| 26 | ≦5 | ≦5 | ≦5 | ≦5 | ≦5 | ≦6 | 10 | ≦5 | ≦5 |
| 29 | ≦5 | ≦5 | 10 | ≦5 | ≦5 | ≦5 | 10 | ≦5 | ≦5 |
| 30 | ≦5 | ≦5 | 10 | ≦5 | ≦5 | ≦5 | 10 | ≦5 | ≦5 |

It can be seen from Table 3 that the compounds are also excellent fungicides.

EXAMPLE 36

Determination of action against algae

(a) *Chlorella vulgaris*

Cultures of *Chlorella vulgaris* which had been grown for 14 days in algae nutrient media are diluted in the ratio 1/200 in the algae nutrient medium. Each of the compounds listed in Table 1 is then added in such an amount as to give a final concentration of 3 mg/liter. After incubating for 6 hours, 10 µl of each culture are withdrawn and added dropwise to algae/agar in order to determine the destructive action. After the cultures have incubated for 14 days under illumination (14 hours of light and 10 hours of darkness, alternately), the growth in the algae medium (determination of growth inhibition) and on the algae/agar (determination of algae-destroying action) is assessed visually.

TABLE 4

Action against *Chlorella vulgaris*

| | GROWTH | |
|---|---|---|
| No. | in the medium | on the agar |
| 2 | — | — |
| 4 | — | — |
| 5 | — | — |
| 6 | — | — |
| 7 | — | — |
| 8 | — | — |
| 14 | — | — |
| 15 | — | — |
| 16 | — | — |
| 17 | — | — |
| 18 | — | — |
| 19 | — | — |
| 20 | — | — |
| 21 | — | — |
| 23 | — | — |
| 24 | — | — |
| 26 | — | — |
| 29 | — | — |
| 30 | — | — |

— = no growth on the agar, 3 ppm have destroyed the algae in 6 hours.

(b) *Enteromorpha intestinalis*

The action against the green alga Enteromorpha, which is the most important in seawter fouling, is investigated in sterile-filtered seawater containing an Erd-Schreiber solution. This solution is composed of a nutrient extract, phosphate and nitrate. The incubation of *Enteromorpha intestinalis* is carried out in a light thermostat at 18° C. under an alternation of 14 hours of light and 10 hours of darkness.

The algae which have been cultured in this way are exposed to the products under investigation for a short time (4 hours) in seawater. The minimum killing concentration (MKC) is determined by taking the algae out of the seawater containing a specific quantity of algicide, after the treatment time in the latter, washing the algae and investigating growth or mortality after incubation in fresh seawater for a further period of 6–8 weeks.

The minimum killing concentration (MKC) indicates the amount of substance required to cause such damage to the algae within a specific time that they can no longer recover in fresh seawater and die out.

For determining the inhibitory concentration (MIC), the algae are kept in seawater containing biocide for the entire duration of the test (concentration tested: 0.5 mg/liter).

TABLE 5

| | Action against *Enteromorpha intestinalis* | |
|---|---|---|
| No. | Destruction, 5 mg/liter | MIC (mg/liter) |
| 2, 4, 5, 6, 7 | yes | 0.5 |

As can be seen from Tables 4 and 5, the compounds have a pronounced algistatic and algicidal action against freshwater algae (for example the treatment of cooling water) and seawater algae (for example protection against growth for anti-fouling paints).

EXAMPLE 37

Determination of action against Artemia salina

The eggs, which are available commercially, are caused to hatch by vigorous aeration. When 2–3 days old, the nauplii are exposed to the products at various concentrations (concentrations tested: 2.5; 1; 0.5 and 0.25 mg/liter) in synthetic seawater, and are observed over a prolonged period of time.

TABLE 6

| | Action against *Artemia salina* (approx. 30–50 nauplii) | | | | | | | | | | | |
|---|---|---|---|---|---|---|---|---|---|---|---|---|
| | 2,5 mg/l | | | 1 mg/l | | | 0,5 mg/l | | | 0,25 mg/l | | |
| Nr. | 6 hours | 24 hours | 48 hours | 6 hours | 24 hours | 48 hours | 6 hours | 24 hours | 48 hours | 6 hours | 24 hours | 48 hours |
| 2 | 2–3 | 3 | 3 | 2 | 3 | 3 | 1–2 | 2–3 | 3 | 0–1 | 2 | 2–3 |
| 4 | 2–3 | 3 | 3 | 2–3 | 3 | 3 | 1–3 | 2–3 | 3 | 0–1 | 2 | 2 |
| 5 | 2–3 | 3 | 3 | 2 | 3 | 3 | 1–2 | 2–3 | 3 | 0–1 | 2 | 2–3 |
| 6 | 2–3 | 3 | 3 | 2 | 3 | 3 | 1–2 | 2–3 | 3 | 1 | 2 | 2–3 |
| 7 | 2–3 | 3 | 3 | 2 | 3 | 3 | 1–2 | 2 | 3 | 0–1 | 2 | 2–3 |
| 24 | 2–3 | 3 | 3 | 2 | 3 | 3 | 1–2 | 2–3 | 3 | 0–1 | 2 | 2–3 |

0 = no change
1 = slight change
1–2 = animals are attacked
2 = animals are strongly attacked
2–3 = animals are nearly all dead
3 = animals are all dead The excellent action of the compounds against the saline crustacean can be seen from Table 6. *Artemia salina* is a relative of the Balanids, which cause considerable problems in the fouling of ships.

Owing to their activity against algae and against crustaceans, the compounds are suitable, inter alia, for incorporation in marine paints. Owing to their broad spectrum of action and their activity against bacteria, algae, fungi and crustaceans, these compounds can be used generally for the protection of materials, for example emulsion paints, anti-fouling paints, water treatment, wood protection, drilling and cutting oils, plastics, the paper industry and others and also disinfection.

EXAMPLE 38

Tests of Effectiveness in Coolant Circuits

The coolant circuits are in the open (natural solar irradiation, entry of dust and effects of weathering) and consist of the following:

(a) a plastics vessel having a volume of 113 liters and an overflow, (b) a pump (21 liters/minute at a delivery head of 3 m) and (c) a cooling tower with oregon (splint) wood, oregon (heart wood), oak, spruce, asbestos cement and PVC boards.

The inflow of fresh water is adjusted so that the loss through spray and evaporation is compensated and the biocides are diluted in a ratio of approximately 1:2 in 24 hours.

The cooling towers are infested by the natural effect of dust and not by deliberate inoculation.

In order to prevent the formation of slime and the growth of algae, the coolant circuit is treated at 100 ppm/week for 3 months and 50 ppm/week for a further 2 months with the following formulation:

4% of Example 2, 15% of dimethylbenzyltetradecylammonium chloride, 8% of isopropanol and 73% of $H_2O$. The test is evaluated by observing fouling on the boards visually.

The circuit which has been treated at 100 ppm/week for the first three months and at 50 ppm for the next two months exhibits no sign of insipient slime formation or growth of algae.

EXAMPLE 39

Growth on Wood

Small blocks of spruce wood, $7 \times 10 \times 10$ mm in size, are dried in vacuo. The small blocks are then vacuum-impregnated by keeping them, in vacuo, in 100 ml of distilled water + biocide for 30 minutes and then subjecting them to a pressure treatment (2 atmospheres gauge by means of compressed air) for 18 hours in the water. The pieces of wood treated in this way are first subjected to leaching in running water and are then dried.

The dried pieces of wood are placed on potato/glucose agar and the wood, as well as the surrounding agar, is inoculated with 0.1 ml of a spore suspension of Aureobasidium pullulans. After incubation at 28° for 4 weeks, the growth is evaluated in accordance with the following rating:

1 = growth on the wood
2 = slight growth on the wood
3 = no growth on the wood
4 = no growth on the wood and an inhibitory zone

| Example | Concentration, % in $H_2O$ | not leached | leached for 5 days |
|---|---|---|---|
| 2 | 0.05 | 4 | 4 |
| | 0.01 | 4 | 4 |
| 6 | 0.05 | 4 | 4 |
| | 0.01 | 4 | 4 |

The excellent action of the compounds in protecting wood—even after storage in water—can be seen from the Table.

EXAMPLE 40

Preparation of Ammonium Stannate (IV) Complexes Having No Organic Radicals in the Stannate Anion (a) Preparation of dimethyl-benzyl-tetradecylammonium pentachlorostannate-(IV):

8.4 g (0.05 mol) of dimethyl-benzyl-tetradecylammonium chloride (Barquat MS 100 ®) are dissolved in 50 ml of chloroform. 13.0 g (0.05 mol) of tin tetrachloride are added to the solution. After the volatile constituents have been moved, a quantitative yield of a viscous oil remains as residue.

(b) Preparation of bis-(dimethyl-benzyl-tetradecylammonium hexachlorostannate-(IV)):

22.0 g (0.06 mol) of dimethyl-benzyl-tetradecylammonium chloride (Barquat MS 100 ®) are dissolved in 50 ml of chloroform. 7.8 g (0.03 mol) of tin tetrachloride are added to the solution. After the volatile constituents have been removed, a quantitative yield of a colourless, crystalline powder of melting point 160°–161° C. remains as residue.

What is claimed is:

1. A compound of formula Ia $$[(R^1)_a(R^2)_bN(R^3)_c(R^4)_d]_n{}^\oplus[(R^7)_3SnX_rY_t]^{n\ominus} \quad \text{(Ia)}$$

in which $R^1$ and $R^2$ are methyl, $R^3$ is benzyl, $R^4$ is $C_8$–$C_{16}$-alkyl, $R^7$ is $C_3$–$C_5$-alkyl, X and Y independently of one another are fluorine, chlorine or bromine, and a, b, c and d are 1, n is 1, r and t are an interger from 0 to 2, the total (r+t) having the value (n+1).

2. A compound of the formula Ia, according to claim 1, in which X and/or Y are fluorine and/or chlorine.

3. A compound according to claim 1, in which $R^7$ is n-butyl.

4. The compound, according to claim 1, dimethyl-benzyl-n-tetradecylammonium- tri-n-butyl-dichlorostannate-(IV).

5. The compound, according to claim 1, dimethyl-benzyl-n-tetradecylammonium- tri-n-butyl-difluorostannate-(IV).

6. A composition containing at least one compound of formula Ia according to claim 1 and an inert carrier.

* * * * *